United States Patent [19]

Page et al.

[11] Patent Number: 4,855,527

[45] Date of Patent: Aug. 8, 1989

[54] OLEFIN OLIGOMERIZATION WITH SURFACE MODIFIED ZEOLITE

[75] Inventors: Nancy M. Page, Yardley, Pa.; Lewis B. Young, Skillman, N.J.

[73] Assignee: Mobil Oil Corporation, New York, N.Y.

[21] Appl. No.: 298,340

[22] Filed: Jan. 13, 1989

Related U.S. Application Data

[63] Continuation of Ser. No. 105,438, Oct. 7, 1987, abandoned.

[51] Int. Cl.$^4$ ................................................ C07C 2/12
[52] U.S. Cl. .................................... 585/527; 585/517; 585/533; 585/329
[58] Field of Search ............... 585/517, 533, 525, 527, 585/327, 329

[56] References Cited

U.S. PATENT DOCUMENTS

| | | | |
|---|---|---|---|
| 2,143,566 | 1/1939 | Moser | 585/517 |
| 2,318,719 | 5/1943 | Schneider et al. | 585/517 |
| 4,359,595 | 11/1982 | Rollman | 585/640 |
| 4,469,912 | 9/1984 | Blewett et al. | 585/525 |
| 4,520,221 | 5/1985 | Chen | 585/517 |
| 4,524,232 | 6/1985 | Chester et al. | 585/517 |
| 4,568,786 | 2/1986 | Hsia Chen et al. | 585/517 |
| 4,658,079 | 4/1987 | Chen | 585/517 |
| 4,675,460 | 6/1987 | Seddon et al. | 585/517 |

FOREIGN PATENT DOCUMENTS

| | | | |
|---|---|---|---|
| 474885 | 11/1937 | United Kingdom | 585/517 |
| 479657 | 2/1938 | United Kingdom | 585/517 |

*Primary Examiner*—Patrick P. Garvin
*Assistant Examiner*—George R. Fourson
*Attorney, Agent, or Firm*—Alexander J. McKillop; Charles J. Speciale; Edward F. Kenahan

[57] ABSTRACT

A process for producing substantially linear hydrocarbons by oligomerizing a lower olefin at elevated temperature and pressure which comprises contacting the lower olefin under oligomerization/polymerization conditions with siliceous acidic ZSM-23 zeolite having Brönsted acid activity; wherein the zeolite has acidic pore activity and wherein the zeolite surface is rendered substantially inactive for acidic reactions. The zeolite surface can be neutralized by a bulky pyridine compound having an effective cross-section larger than the zeolite pore. The preferred deactivating agent is 2,4,6-collidine, which may be applied to the zeolite as a pretreatment or added with olefin feed in a continuous process.

7 Claims, No Drawings

OLEFIN OLIGOMERIZATION WITH SURFACE MODIFIED ZEOLITE

This is a continuation of copending application Ser. No. 105,438, filed on Oct. 7, 1987, now abandoned.

FIELD OF THE INVENTION

The invention relates to a process for producing high molecular weight hydrocarbons from a lower olefin feedstock by employing a shape selective crystalline silicate catalyst which is surface inactivated.

BACKGROUND OF THE INVENTION

Recent work in the field of olefin upgrading has resulted in a catalytic process for converting lower olefins to heavier hydrocarbons. Heavy distillate and lubricant range hydrocarbons can be synthesized over ZSM-5 type catalysts at elevated temperature and pressure to provide a product having substantially linear molecular conformations due to the ellipsoidal shape selectivity of certain medium pore catalysts.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. Particular interest is shown in a technique developed by Garwood, et al., as disclosed in European Patent Application No. 83301391.5, published Sept. 29, 1983. In U.S. Pat. Nos. 4,150,062; 4,211,640; 4,227,992; and 4,547,613 Garwood, et al. disclose the operating conditions for the Mobil Olefin to Gasoline/Distillate (MOGD) process for selective conversion of $C_3^+$ olefins to mainly aliphatic hydrocarbons.

In the process for catalytic conversion of olefins to heavier hydrocarbons by catalytic oligomerization using a medium pore shape selective acid crystalline zeolite, process conditions can be varied to favor the formation of hydrocarbons of varying molecular weight. At moderate temperature and relatively high pressure, the conversion conditions favor $C_{10}^+$ aliphatic product. Lower olefinic feedstocks containing $C_2$-$C_8$ alkenes may be converted; however, the distillate mode conditions do not convert a major fraction of ethylene. A typical reactive feedstock consists essentially of $C_3$-$C_6$ mono-olefins, with varying amounts of non-reactive paraffins and the like being acceptable components.

Although it is known to use basic materials to deactivate the Brönsted acid sites on the surface of aluminosilicate catalysts (see U.S. Pat. No. 4,520,221 and U.S. Pat. No. 4,568,786, Chen, et al., incorporated herein by reference), the basic materials employed are bulky amines, such as di-tert-butyl pyridine.

Shape-selective oligomerization, as it applies to the conversion of $C_2$-$C_{10}$ olefins over ZSM-5, is known to produce higher olefins up to $C_{30}$ and higher. As reported by Garwood in "Intrazeolite Chemistry 23", (Amer. Chem. Soc., 1983), reaction conditions favoring higher molecular weight product are low temperature (200°-260° C.), elevated pressure (about 2000 kPa or greater), and long contact time (less than 1 WHSV). The reaction under these conditions proceeds through the acid-catalyzed steps of (1) oligomerization, (2) isomerization-cracking to a mixture of intermediate carbon number olefins, and (3) interpolymerization to give a continuous boiling product containing all carbon numbers. The channel systems of medium pore catalysts impose shape-selective constraints on the configuration of the large molecules, accounting for the differences with other catalysts.

The desired oligomerization-polymerization products include $C_{10}^+$ substantially linear aliphatic hydrocarbons. This catalytic path for propylene feed provides a long chain which may have one or more lower alkyl (e.g., methyl) substituents along the straight chain.

The final molecular configuration is influenced by the pore structure of the catalyst. For the higher carbon numbers, the structure is primarily a methyl-branched straight olefinic chain, with the maximum cross-section of the chain limited by the dimension of the largest zeolite pore. Although emphasis is placed on the normal 1-alkenes as feedstocks, other lower olefins, such as 2-butene or isobutylene, are readily employed as starting materials due to rapid isomerization over the acidic zeolite catalysts. At conditions chosen to maximize heavy distillate and lubricant range products ($C_{20}^+$), the raw aliphatic product is essentially mono-olefinic. Overall branching is not extensive and may occur at spaced positions within the molecule.

The viscosity index of a hydrocarbon lube oil is related to its molecular configuration. Extensive branching in a molecule usually results in a low viscosity index. It is believed that two modes of oligomerization/polymerization of olefins can take place over acidic zeolites, such as HZSM-5. One reaction sequence takes place at Bronsted acid sites inside the channels or pores, producing essentially linear materials. The other reaction sequence occurs on the outer surface, producing more branched material. By decreasing the surface acid activity of such zeolites, fewer highly branched products with low VI are obtained.

Several techniques may be used to increase the relative ratio of intra-crystalline acid sites to surface active sites. This ratio increases with crystal size due to geometric relationship between volume and superficial surface area. Deposition of carbonaceous materials by coke formation can also shift the effective ratio, as disclosed in U.S. Pat. No. 4,547,613. However, enhanced effectiveness is observed where the surface acid sites of small crystal zeolites are reacted with a chemisorbed trialkyl pyridine, such as collidine.

It is a main object of this invention to provide an improved process for upgrading olefins to valuable lubricant quality product. Significantly improved linearity can be achieved by employing a catalyst comprising a medium pore shape selective siliceous zeolite with a surface that has been substantially inactivated with a sterically hindered nitrogenous base, such as a trialkyl pyridine compound.

SUMMARY OF THE INVENTION

It has been discovered that when a surface-inactivated, but internally active, ZSM-23 metallosilicate zeolite catalyst is employed in olefin oligomerization, the reaction yields a high quality, essentially linear oligomer stock which can be efficiently converted to high VI lube oils. The catalyst can be surface inactivated in situ by cofeeding a sterically hindered basic amine compound with the olefinic feedstock, or the novel catalyst can be treated in a separate step prior to olefin oligomerization.

Unless otherwise specified, metric units and parts-by-weight (pbw) are utilized in the description and examples.

DESCRIPTION OF THE PREFERRED EMBODIMENTS

Recent developments in zeolite technology have provided a group of medium pore siliceous materials having similar pore geometry. Prominent among these intermediate pore size zeolites is ZSM-23, which may be synthesized with Bronsted acid active sites by incorporating a tetrahedrally coordinated metal, such as Al, Ga, or Fe, within the zeolitic framework. These medium pore zeolites are favored for acid catalysis; however, the advantages of ZSM-23 structures may be utilized by employing highly siliceous materials or crystalline metallosilicate having one or more tetrahedral species having varying degrees of acidity. ZSM-23 crystalline structure is readily recognized by its X-ray diffraction pattern, which is described in U.S. Pat. No. 4,076,842 (Rubin, et al.), incorporated by reference.

The shape-selective oligomerization/polymerization catalysts preferred for use herein include the crystalline aluminosilicate zeolites having a silica-to-alumina molar ratio of at least 12, a constraint index of about 8 to 10, and acid cracking activity (alpha value) of about 10-300. A suitable shape selective medium pore catalyst for fixed bed is a small crystal H-ZSM-23 zeolite having alpha value of about 25, with alumina binder in the form of cylindrical extrudates of about 1-5 mm. The preferred catalyst consists essentially of ZSM-23 having a crystallite size of about 0.02 to 2 microns, with framework metal synthesized as gallo-silicate, ferrosilicate, and/or aluminosilicate. These zeolites have a pore size of 4.5 X 5.6 Angstroms, such as to freely sorb normal hexane. In addition, the structure must provide constrained access to larger molecules.

It is generally understood that the proportion of internal acid sites relative to external acid sites increases with larger crystal size. However, the smaller crystallites, usually less than 0.1 micron, are preferred for diffusion-controlled reactions, such as oligomerization, polymerization, etc. Accordingly, it may be required to neutralize more than 15% of the total Brönsted acid sites by chemisorption of the basic deactivating agent.

The degree of steric hindrance should also be considered in the choice of the basic nitrogen compounds, especially the bulky trialkyl pyridine species having alkyl groups of 1 to 4 carbon atoms. Although the selected organonitrogen compound must be bulky enough to prevent infusion of said compound into the internal pores of the catalyst, excessive steric hindrance may prevent effective or complete interaction between the surface Bronsted acid site and the selected basic species.

Catalysts of low surface activity can be obtained by using medium pore, shape selective ZSM-23 zeolites of small crystal size that have been deactivated by one or more trialkyl pyridine compounds, such as 2,4,6-collidine (2,4,6-trimethyl pyridine, gamma-collidine). These compounds all must have a minimum cross-section diameter greater than the effective pore size of the zeolite to be treated; i.e., greater than 5 Angstroms.

EXAMPLE I

Aluminosilicate H-ZSM-23 extrudate (65% zeolite, 35% alumina binder) is loaded into a metal pressurized reactor and calcined overnight at 500° C. The catalyst is then used to oligomerize propylene to intermediate molecular weight olefins. Various temperatures and feed rates are employed. These results are summarized in Table 1.

TABLE 1

| Propylene Oligomerization with HZSM-23 | | | | | |
|---|---|---|---|---|---|
| Run No. | $C_3=$ WHSV | Temp. °C. | $C_{12}+$ Select. wt. %[a] | Branching Index[b] | Branching Methyls[b] per $C_{15}$ |
| 1-A | 1.0 | 160 | 61.5 | 51.7 | 3.7 |
| 1-B | 0.5 | 160 | 73.7 | 51.4 | 3.6 |
| 1-C | 0.5 | 200 | 78.6 | 54.7 | 4.0 |
| 1-D | 1.0 | 200 | 81.7 | 55.1 | 4.2 |
| 1-E | 1.0 | 225 | 78.5 | 52.3 | 3.9 |

[a] In crude reaction product
[b] In $C_{12}+$ fraction

The determination of Branching Index is a useful and sensitive method practiced by those skilled in the arts to which the present invention applies and used to quantitatively assess the degree of linearity of a molecule or molecular mixture. The index is determined as follows: the C6 and C9 oligomers are first removed from the sample and the C12+ fraction is hydrogenated using Pd/charcoal catalyst in acetic acid. The hydrogenated sample is extracted from the acetic acid into deutrochloroform and the 1H NMR spectrum determined. The branching index is defined as the ratio of the intensity (area) of the resonance due to CH3 (0.7-1.0 ppm) divided by the sum of the intensities (areas) of the resonances due to CH3 (0.7.-1.0 ppm) and CH2 (1.1-1.8 ppm). The number of methyl groups per molecule is defined by the equation $$Me/molecule = B.I.*(n+1)/150$$

where B. I. = branching index as defined above and n = carbon number of the fraction of interest.

This calculated number of methyls per molecule includes the two terminal methyl groups. Therefore, to determine the actual number of mid-chain ethyl groups, these two terminal methyl groups must be subtracted from the total methyl/molecule value calculated.

EXAMPLE II

The catalyst used in Example I is calcined in the reactor overnight at 500° C. The calcined catalyst is then cooled to room temperature in the reactor, and a solution containing 1 gram 2,6-di-t-butyl pyridine per 100 ml pentane is passed over the catalyst until a total of 6 ml of deactivating solution per gram of catalyst has been used. Following this treatment, the catalyst is purged with nitrogen for one hour at room temperature, then the reactor temperature is slowly increased and reaction of propylene begun. During the reaction of propylene, a small amount of 2,6-di-t-butyl pyridine (DTBP) solution is co-fed to maintain surface deactivation. The results of these screening reactions are summarized in Table 2.

TABLE 2

Propylene Oligomerization with 2,6-DTBP Modified ZSM-23

| Run No. | $C_3=$ WHSV | 2,6-DTBP ppm | Temp. °C. | $C_{12}+$ Select. wt. %[a] | Branching Index[b] | Branching Methyls[b] per $C_{15}$ |
|---------|------|------|-----|------|------|-----|
| 2-A | 1.0 | 400 | 175 | 18.4 | 40.0 | 2.1 |
| 2-B | 0.5 | 800 | 200 | 43.8 | 39.4 | 2.3 |
| 2-C | 1.0 | 400 | 200 | 32.2 | 40.7 | 2.3 |
| 2-D | 0.5 | 800 | 220 | 50.4 | 41.9 | 2.6 |

[a] In crude reaction product
[b] In $C_{12}+$ fraction

EXAMPLE III

H-ZSM-23, prepared as in Example I is treated with deactivating solution as in Example II, except that the basic component is 2,4,6-collidine. A small co-feed of 2,4,6-collidine solution is continued during reaction to maintain surface deactivation. Results of these reactions are summarized in Table 3.

TABLE 3

Propylene Oligomerization with 2,4,6-Collidine Modified ZSM-23

| Run No. | $C_3=$ WHSV | 2,4,6- Coll., ppm | Temp. °C. | $C_{12}+$ Select. wt. %[a] | Branching Index[b] | Branching Methyls[b] per $C_{15}$ |
|---------|------|------|-----|------|------|-----|
| 3-A | 0.5 | 200 | 200 | 24.7 | 35.5 | 1.8 |
| 3-B | 0.25 | 400 | 200 | 35.1 | 34.9 | 1.7 |
| 3-C | 0.25 | 400 | 212 | 39.7 | 37.2 | 2.0 |
| 3-D | 0.25 | 400 | 225 | 33.5 | 37.6 | 2.0 |
| 3-E | 0.25 | 200 | 225 | 36.4 | 40.4 | 2.3 |

[a] In crude reaction product
[b] In $C_{12}+$ fraction

The above experimental runs are conducted at a pressure of about 3500–4300Pa (500–600 psig.). Comparative examples run at equivalent space velocity and temperature (e.g., 0.5 WHSV and 200° C.) show significant improvement in product linearity employing the trialkylpyridine agent.

EXAMPLE IV

Propylene is contacted according to the procedure of Example I with 2,4,6-collidine modified HZSM-23 in a flow reactor at 200° C. at the rate of 0.25 g propylene/g zeolite/hr. The crude product is distilled to obtain a $C_{15}+$ fraction. The $C_{15}+$ fraction is contacted with $BF_3$/70% aqueous phosphoric acid catalyst at room temperature for about 4 hours. The crude product, containing about 75 wt % of $C_{25}+$ lube range hydrocarbon is stripped to remove the $C_{24}-$ hydrocarbons. The viscosity index of the $C_{25}+$ fraction is 128; the 100° C. viscosity is 8.2 cSt.

In the multistage process 70% aqueous phosphoric acid in combination with $BF_3$ is superior to other $BF_3$/promoter combinations for converting $C_{10}-C_{20}$ intermediate olefins to lube-range hydrocarbons.

While the invention has been described by specific examples and embodiments, there is no intent to limit the inventive concept except as set forth in the following claims.

EXAMPLE V 15.4 gms HZSM-5 (65% zeolite, 35% alumina binder) are treated with 0.18 grams 2,4,6-collidine in approximately 50 cc pentane. This represents 0.25 moles amine per mole of acid in the zeolite. The pentane is allowed to evaporate at room temperature and the surface modified catalyst charged to a fixed bed tubular reactor at superatmospheric pressure. Propylene is metered to the reactor and a solution of 1 gram 2,4,6-collidine in 500 ml pentane is also metered to the reactor. The rate is controlled to give approximately 0.2 mmoles amine per mole H+in the zeolite per hour. Reaction temperature is adjusted in an effort to achieve 50% propylene conversion.

| | |
|---|---|
| TEMP | 205° C. |
| PRESSURE | 3600 kPa (500 psig) |
| $C_3=$ WHSV, HR-1 | 0.21 |
| DEACTIVATING AGENT IN FEED | 65 ppm |
| $C_3=$ CONV, WT % | 55.0 |
| C12+ SELECTIVITY | 20.1% |
| C15+ | 5.9 |
| BRANCHING INDEX | 32.8 |
| BRANCHING METHYLS PER C15 | 1.5 |

EXAMPLE VI

Example V is repeated, except that 15.4 gms ZSM-5 (65% zeolite, 35% alumina binder) are treated with a solution containing 0.28 grams, 2,6-di-t-butylpyridine in pentane. (0.25 mols amine per mole H+ in the zeolite). Comparative results are summarized as follows:

| | |
|---|---|
| TEMP | 145° C. |
| PRESSURE | 3600 kPa |
| $C_3=$ WHSV, HR$^{-1}$ | 0.22 |
| AMINE IN FEED | 100 ppm |
| $C_3=$ CONVERSION, WT % | 59.1 |
| C12+ SELECTIVITY | 9.8 |
| BRANCHING INDEX | 38.4 |
| BRANCHING METHYLS PER C15 | 2.1 |

EXAMPLE VII

Example V is repeated, except 15.4 gms HZSM-23 (65% zeolite, 35% alumina binder) are treated with 0.088 gms, 2,4,6-collidine in approximately 50 ml pentane. (0.25 moles amine per mole H+ in the zeolite). Screening is carried at various conditions with an effort to achieve 50% propylene conversion. Results are summarized as follows:

| | |
|---|---|
| TEMP | 175° C. |
| PRESSURE | 3600 kPa |
| $C_3=$ WHSV, HR-1 | 0.21 |
| AMINE IN FEED | 200 ppm |
| $C_3=$ CONVERSION, WT % | 57.7 |
| C12+ SELECTIVITY | 22.0 |
| BRANCHING INDEX | 30.5 |
| BRANCHING METHYLS PER C15 | 1.25 |

EXAMPLE VIII

Example VII is repeated, except 15.4 gms ZSM-23 (65% zeolite, 35% alumina binder) are treated with 0.14 gms, 2,6-di-t-butylpyridine in approximately 50 ml pentane. (0.25 moles amine per mole H+ in the zeolite). Results are summarized as follows:

| | |
|---|---|
| TEMP | 145° C. |
| PRESSURE | 3600 kPa |
| C3=WHSV, HR-1 | 0.21 |
| AMINE IN FEED | 50 ppm |
| C3= CONVERSION, WT % | 59.0 |
| C12+ SELECTIVITY | 21.6 |
| BRANCHING INDEX | 31.4 |
| BRANCHING METHYLS PER C15 | 1.35 |

We claim:

1. A process for producing substantially linear hydrocarbons by oligomerizing a lower olefin at elevated temperature and pressure which comprises
contacting the lower olefin under polymerization conditions with siliceous acidic ZSM-23 zeolite having Bronsted acid activity; wherein said zeolite has acidic pore activity and wherein the zeolite surface is rendered substantially inactive for acidic reactions, said zeolite surface being neutralized by contacting HZSM-23 with 2,4,6-collidine.

2. The process of claim 1 wherein the zeolite is an aluminosilicate having a silica-to-alumina molar ratio of at least 12.

3. The process of claim 1 wherein said olefin comprises $C_3$ to $C_6$ lower olefin.

4. A multi-stage process for producing high viscosity index lubricating oils from lower olefin feed which comprises
contacting the lower olefins in a primary reaction zone under conditions of elevated temperature and pressure with a siliceous ZSM-23 zeolite catalyst having Bronsted acid activity; wherein said zeolite has acidic pore activity and wherein the zeolite surface is rendered substantially inactive for acidic reactions, said zeolite surface being neutralized by contacting HZSM-23 with 2,4,6-collidine, thereby producing substantially linear $C_{10}{}^+$ olefins; and
contacting at least a portion of the primary stage effluent in a secondary reaction zone with an acid catalyst to effectively polymerize the $C_{10}{}^+$ hydrocarbons.

5. The process of claim 4 wherein the zeolite catalyst contains ZSM-23 having an alpha value of about 10 to 300 prior to surface neutralization.

6. The process of claim 4 wherein the acid catalyst in the secondary reaction zone comprises $BF_3$ and phosphoric acid.

7. The process of claim 4 wherein the lower olefin feed consists essentially of $C_3$ to $C_6$ olefin and the primary stage effluent comprises substantially linear $C_{10}$ to $C_{20}$ olefins.

* * * * *